United States Patent
Hale et al.

(10) Patent No.: US 7,462,612 B2
(45) Date of Patent: *Dec. 9, 2008

(54) PYRIDINE INHIBITORS OF ERK2 AND USES THEREOF

(75) Inventors: Michael Hale, Bedford, MA (US); Gabriel Martinez-Botella, West Roxbury, MA (US); Qing Tang, Acton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 527 days.

This patent is subject to a terminal disclaimer.

(21) Appl. No.: 11/089,701

(22) Filed: Mar. 25, 2005

(65) Prior Publication Data

US 2006/0019953 A1   Jan. 26, 2006

Related U.S. Application Data

(60) Provisional application No. 60/556,766, filed on Mar. 26, 2004.

(51) Int. Cl.
C07D 401/04 (2006.01)
C07D 401/12 (2006.01)
A61K 31/497 (2006.01)
A61K 31/4439 (2006.01)

(52) U.S. Cl. .............. 514/235.5; 514/253.09; 514/318; 514/333; 514/343; 544/124; 544/364; 546/193; 546/256; 546/279.1

(58) Field of Classification Search ........... 544/124, 544/364; 514/235.5, 253.09, 318, 333, 343; 546/193, 256, 279.1
See application file for complete search history.

(56) References Cited

U.S. PATENT DOCUMENTS 5,776,954 A * 7/1998 de Laszlo et al. .......... 514/340
7,354,939 B2 * 4/2008 Martinez-Botella et al. . 514/343

FOREIGN PATENT DOCUMENTS

| WO | WO95/18122 | 7/1995 |
| WO | WO01/57022 | 8/2001 |
| WO | WO03/091246 | 11/2003 |
| WO | WO2004/058762 | 7/2004 |
| WO | WO2004/072063 | 8/2004 |

OTHER PUBLICATIONS

Simone, Oncology: Introduction, Cecil Textbook of Medicine, 20th Edition, vol. 1, pp. 1004-1010, 1996.*
Lutzen, et al., "Synthesis of Differently Disubstituted 2, 2'—Bipyridines by a Modified Negishi Cross-Coupling Reaction" *Eur. J. Org. Chem.* 3948-3957, 2003.
Martineau, et al., "New Ruthenium Complexes with 4-(1H-Pyrrol-1-yl)-Substituted Polypyridine Ligands—Electrochemical and Spectroscopic Properties" *Eur. J. Org. Chem.* 3984-3986, 2004.
International Search Report issued for corresponding PCT application PCT/US2005/010204.

* cited by examiner

*Primary Examiner*—Deepak Rao
(74) *Attorney, Agent, or Firm*—Daniel A. Pearson

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

15 Claims, No Drawings

PYRIDINE INHIBITORS OF ERK2 AND USES THEREOF

CROSS REFERENCE TO RELATED APPLICATION

This application claims priority to U.S. Provisional Patent Application 60/556,766 filed Mar. 26, 2004, the entire contents of which are hereby incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors useful as therapeutic agents.

ERK Kinase

ERK2 is a widely distributed protein kinase that achieves maximum activity when both Thr183 and Tyr185 are phosphorylated by the upstream MAP kinase kinase, MEK1 (Anderson et al., 1990, Nature 343, 651; Crews et al., 1992, Science 258, 478). Upon activation, ERK2 phosphorylates many regulatory proteins, including the protein kinases Rsk90 (Bjorbaek et al., 1995, J. Biol. Chem. 270, 18848) and MAPKAP2 (Rouse et al., 1994, Cell 78, 1027), and transcription factors such as ATF2 (Raingeaud et al., 1996, Mol. Cell Biol. 16, 1247), Elk-1 (Raingeaud et al. 1996), c-Fos (Chen et al., 1993 Proc. Natl. Acad. Sci. USA 90, 10952), and c-Myc (Oliver et al., 1995, Proc. Soc. Exp. Biol. Med. 210, 162). ERK2 is also a downstream target of the Ras/Raf dependent pathways (Moodie et al., 1993, Science 260, 1658) and relays the signals from these potentially oncogenic proteins. ERK2 has been shown to play a role in the negative growth control of breast cancer cells (Frey and Mulder, 1997, Cancer Res. 57, 628) and hyperexpression of ERK2 in human breast cancer has been reported (Sivaraman et al., 1997, J. Clin. Invest. 99, 1478). Activated ERK2 has also been implicated in the proliferation of endothelin-stimulated airway smooth muscle cells, suggesting a role for this kinase in asthma (Whelchel et al., 1997, Am. J. Respir. Cell Mol. Biol. 16, 589).

Overexpression of receptor tyrosine kinases such as EGFR and ErbB2 (Arteaga C L, 2002, Semin Oncol. 29, 3-9; Eccles S A, 2001, J Mammary Gland Biol Neoplasia 6:393-406; Mendelsohn J & Baselga J, 2000, Oncogene 19, 6550-65), as well as activating mutations in the Ras GTPase proteins (Nottage M & Siu L L, 2002, Curr Pharm Des 8, 2231-42; Adjei A A, 2001, J Natl Cancer Inst 93, 1062-74) or B-Raf mutants (Davies H. et al., 2002, Nature 417, 949-54; Brose et al., 2002, Cancer Res 62, 6997-7000) are major contributors to human cancer. These genetic alterations are correlated with poor clinical prognosis and result in activation of the Raf-1/2/3-MEK1/2-ERK1/2 signal transduction cascade in a broad panel of human tumors. Activated ERK (i.e. ERK1 and/or ERK2) is a central signaling molecule that is associated with the control of proliferation, differentiation, anchorage-independent cell survival, and angiogenesis, contributing to a number of processes that are important for the formation and progression of malignant tumors. These data show that an ERK1/2 inhibitor will exert pleiotropic activity, including proapoptotic, anti-proliferative, anti-metastatic and anti-angiogenic effects, and will offer a therapeutic opportunity against a very broad panel of human tumors.

There is a growing body of evidence that implicates constitutive activation of the ERK MAPK pathway in the oncogenic behavior of select cancers. Activating mutations of Ras are found in ~30% of all cancers, with some, such as pancreatic (90%) and colon (50%) cancer, harboring particularly high mutation rates. Ras mutations have also been identified in 9-15% of melanomas, but B-Raf somatic missense mutations conferring constitutive activation are more frequent and are found in 60-66% malignant melanomas. Activating mutations of Ras, Raf and MEK are able to oncogenically transform fibroblasts in vitro, and Ras or Raf mutations in conjunction with the loss of a tumor suppressor gene (e.g. p16INK4A) can cause spontaneous tumor development in vivo. Increased ERK activity has been demonstrated in these models and has also been widely reported in appropriate human tumors. In melanoma, high basal ERK activity resulting from either B-Raf or N-Ras mutations or autocrine growth factor activation is well documented and is associated with rapid tumor growth, increased cell survival and resistance to apoptosis. Additionally, ERK activation is considered a major driving force behind the highly metastatic behavior of melanoma associated with increased expression of both extracellular matrix degrading proteases and invasion-promoting integrins as well as the downregulation of E-cadherin adhesion molecules that normally mediate keratinocyte interactions to control melanocyte growth. These data taken together, indicate ERK as a promising therapeutic target for the treatment of melanoma, a currently untreatable disease.

Rock Kinase

Another kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell Biol.* 1996, 16, 5313-5327; Amano et al., *Science* 1997, 275, 1308-1311; Ishizaki et al., *FEBS Lett.* 1997, 404, 118-124) and in downregulation of myosin phosphatase (Kimura et al., *Science* 1996, 273, 245-248), platelet activation (Kiages et al., *J. Cell. Biol.* 1999, 144, 745-754), aortic smooth muscle contraction by various stimuli (Fu et al., *FEBS Lett.* 1998, 440, 183-187), thrombin-induced responses of aortic smooth muscle cells (Seasholtz et al., *Cir. Res.* 1999, 84, 1186-1193), hypertrophy of cardiomyocytes (Kuwahara et al., *FEBS Lett.,* 1999, 452, 314-318), bronchial smooth muscle contraction (Yoshii et al., *Am. J. Respir. Cell Mol. Biol.* 1999, 20, 1190-1200), smooth muscle contraction and cytoskeletal reorganization of non-muscle cells (Fukata et al., *Trends in Pharm. Sci* 2001, 22, 32-39), activation of volume-regulated anion channels (Nilius et al., *J. Physiol.* 1999, 516, 67-74), neurite retraction (Hirose et al., *J. Cell. Biol.* 1998, 141, 1625-1636), neutrophil chemotaxis (Niggli, *FEBS Lett.* 1999, 445, 69-72), wound healing (Nobes and Hall, *J. Cell. Biol.* 1999, 144, 1235-1244), tumor invasion (Itoh et al., *Nat. Med.* 1999, 5, 221-225) and cell transformation (Sahai et al., *Curr. Biol.* 1999, 9, 136-145). Accordingly, the development of inhibitors of ROCK kinase would be useful as therapeutic agents for the treatment of disorders mediated by the ROCK kinase pathway.

Accordingly, there is a great need to develop compounds useful as inhibitors of protein kinases. In particular, it would be desirable to develop compounds that are useful as inhibitors of ERK2 and ROCK protein kinases particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of one or more of ERK2 and ROCK protein kinases. These compounds have the general formula I:

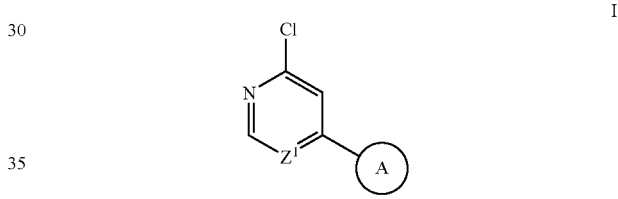

or a pharmaceutically acceptable salt thereof, wherein Ring A and $Z^1$ are as described herein.

These compounds and pharmaceutically acceptable compositions thereof are useful for treating or preventing a variety of diseases, disorders or conditions, including, but not limited to, heart disease, diabetes, Alzheimer's disease, immunodeficiency disorders, inflammatory diseases, allergic diseases, autoimmune diseases, destructive bone disorders such as osteoporosis, proliferative disorders, infectious diseases, immunologically-mediated diseases, neurodegenerative or neurological disorders, or viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation.

It is a further objective of this invention to provide methods for making the compounds and compositions of this invention.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

1. General Description of Compounds of the Invention:

The present invention relates to a compound of formula I:

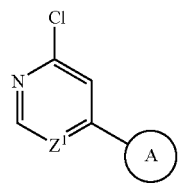

I or a pharmaceutically acceptable salt thereof, wherein:

Ring A is a pyrrole ring optionally substituted at the 1-position with $R^z$ and substituted with:
  (i) zero, one, or two $R^y$ groups, and
  (ii) $QR^2$;

each $R^y$ is independently selected from an optionally substituted $C_{1-6}$ aliphatic group, Ar, CN, $NO_2$, halogen, $N(R)_2$, SR, or OR, provided that two $R^y$ groups are not simultaneously Ar;

$R^z$ is R, C(O)R, C(O)OR, or $SO_2R$;

$Z^1$ is N or C-$T_{(m)}R^1$;

T is a valence bond or a $C_{1-6}$ alkylidene chain;

m is zero or one;

$R^1$ is selected from CN, halogen, $OR^3$, $SR^3$, $N(R)R^3$, or $R^4$;

Q is selected from a valence bond, —C(O)N(R)—, —$SO_2$N(R)—, —$SO_2$—, —N(R)C(O)N(R)—, —N(R)C(O)—, —N(R)$SO_2$—, —N(R)$SO_2$N(R)—, —N(R)C(O)O—, —C(O)—, or —C(O)O—;

$R^2$ is selected from halogen, CN, $(CH_2)_yR^5$, $(CH_2)_yCH(R^5)_2$, $(CH_2)_yCH(R^6)CH(R^5)_2$, $(CH_2)_yN(R^4)_2$, or $N(R^4)(CH_2)_yN(R^4)_2$;

each $R^3$ is independently selected from R or Ar;

each y is independently 0-6;

each Ar is independently selected from an optionally substituted 3-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;

each R is independently selected from hydrogen or an optionally substituted $C_{1-6}$ aliphatic group, or:
  two R on the same nitrogen atom are taken together with the nitrogen atom attached thereto to form a 4-8 membered saturated, partially unsaturated, or fully unsaturated ring having 1-4 heteroatoms independently selected from nitrogen, oxygen, or sulfur;

each $R^4$ is independently selected from $R^3$, $C(O)R^3$, $CO_2R^3$, $CON(R^3)_2$, $SO_2R^3$;

each $R^5$ is independently selected from $R^3$, $OR^3$, $CO_2R^3$, $(CH_2)_yN(R^4)_2$, $N(R^4)_2$, $N(R)C(O)R^3$, $N(R)CON(R^3)_2$, $CON(R^3)_2$, $SO_2R^3$, $N(R)SO_2R^3$, $C(O)R^3$, CN, or $SO_2N(R^3)_2$;

$R^6$ is selected from $R^3$, $(CH_2)_wOR^3$, $(CH_2)_wN(R^4)_2$, or $(CH_2)_w SR^3$; and each w is independently selected from 0-4.

2. Compounds and Definitions:

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; R$^\circ$; OR$^\circ$; SR$^\circ$; 1,2-methylene-dioxy; 1,2-ethylenedioxy; phenyl (Ph) optionally substituted with R$^\circ$; —O(Ph) optionally substituted with R$^\circ$; (CH$_2$)$_{1-2}$(Ph), optionally substituted with R$^\circ$; CH=CH(Ph), optionally substituted with R$^\circ$; NO$_2$; CN; N(R$^\circ$)$_2$; NR$^\circ$C(O)R$^\circ$; NR$^\circ$C(O)N(R$^\circ$)$_2$; NR$^\circ$CO$_2$R$^\circ$; —NR$^\circ$NR$^\circ$C(O)R$^\circ$; NR$^\circ$NR$^\circ$C(O)N(R$^\circ$)$_2$; NR$^\circ$NR$^\circ$CO$_2$R$^\circ$; C(O)C(O)R$^\circ$; C(O)CH$_2$C(O)R$^\circ$; CO$_2$R$^\circ$; C(O)R$^\circ$; C(O)N(R$^\circ$)$_2$; OC(O)N(R$^\circ$)$_2$; S(O)$_2$R$^\circ$; SO$_2$N(R$^\circ$)$_2$; S(O)R$^\circ$; NR$^\circ$SO$_2$N(R$^\circ$)$_2$; NR$^\circ$SO$_2$R$^\circ$; C(=S)N(R$^\circ$)$_2$; C(=NH)—N(R$^\circ$)$_2$; or (CH$_2$)$_{0-2}$NHC(O)R$^\circ$ wherein each independent occurrence of R$^\circ$ is selected from hydrogen, optionally substituted C$_{1-6}$ aliphatic, an unsubstituted 5-6 membered heteroaryl or heterocyclic ring, phenyl, O(Ph), or CH$_2$(Ph), or, notwithstanding the definition above, two independent occurrences of R$^\circ$, on the same substituent or different substituents, taken together with the atom(s) to which each R$^\circ$ group is bound, form a 3-8 membered cycloalkyl, heterocyclyl, aryl, or heteroaryl ring having 0-3 heteroatoms independently selected from nitrogen, oxygen, or sulfur. Optional substituents on the aliphatic group of R$^\circ$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R$^\circ$ is unsubstituted.

An aliphatic or heteroaliphatic group or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring are selected from R$^+$, N(R$^+$)$_2$, C(O)R$^+$, CO$_2$R$^+$, C(O)C(O)R$^+$, C(O)CH$_2$C(O)R$^+$, SO$_2$R$^+$, SO$_2$N(R$^+$)$_2$, C(=S)N(R$^+$)$_2$, C(=NH)—N(R$^+$)$_2$, or NR$^+$SO$_2$R$^+$; wherein R$^+$ is hydrogen, an optionally substituted C$_{1-6}$ aliphatic, optionally substituted phenyl, optionally substituted O(Ph), optionally substituted CH$_2$(Ph), optionally substituted (CH$_2$)$_{1-2}$(Ph); optionally substituted CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of $R^o$ (or $R^+$, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of $R^o$ (or $R^+$, or any other variable similarly defined herein) are taken together with the atom(s) to which each variable is bound include, but are not limited to the following: a) two independent occurrences of $R^o$ (or $R^+$, or any other variable similarly defined herein) that are bound to the same atom and are taken together with that atom to form a ring, for example, $N(R^o)_2$, where both occurrences of $R^o$ are taken together with the nitrogen atom to form a piperidin-1-yl, piperazin-1-yl, or morpholin-4-yl group; and b) two independent occurrences of $R^o$ (or $R^+$, or any other variable similarly defined herein) that are bound to different atoms and are taken together with both of those atoms to form a ring, for example where a phenyl group is substituted with two occurrences of $OR_o$

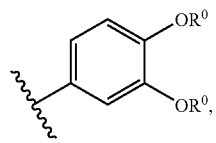

these two occurrences of $R^o$ are taken together with the oxygen atoms to which they are bound to form a fused 6-membered oxygen containing ring:

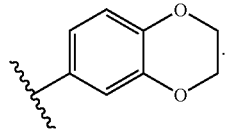

It will be appreciated that a variety of other rings can be formed when two independent occurrences of $R^o$ (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

According to one embodiment, the present invention relates to a compound of formula I wherein $Z^1$ is $C\text{-}T_{(m)}R^1$, thus forming a pyridine ring. Accordingly, the present invention relates to a compound of formula I-a:

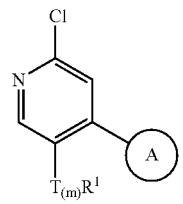

I-a or a pharmaceutically acceptable salt thereof, wherein Ring A, T, m, and $R^1$ are as defined above.

According to another embodiment, the present invention relates to a compound of formula I wherein $Z^1$ is N, thus forming a pyrimidine ring. Accordingly, the present invention relates to a compound of formula I-b:

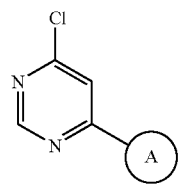

I-b or a pharmaceutically acceptable salt thereof, wherein Ring A is as defined above.

According to one embodiment, the $R^1$ group of either of formula I or I-a is selected from hydrogen, $N(R)R^3$, $OR^3$, 3-6 membered carbocyclyl, or an optionally substituted group selected from $C_{1-6}$ aliphatic or a 5-6 membered aryl ring having 0-4 heteroatoms independently selected from nitrogen, oxygen, or sulfur. When $R^1$ is an optionally substituted phenyl or $C_{1-6}$ aliphatic group, exemplary substituents on the phenyl or $C_{1-6}$ aliphatic group include $R^o$, halo, nitro, $OR_o$, and amino. Another embodiment of the present invention relates to a compound of either of formula I or I-a, wherein $R^1$ is hydrogen, methyl, ethyl, propyl, cyclopropyl, cyclohexyl, phenyl, pyridyl, $CH_2OCH_3$, $CH_2OH$, $NH_2$, $NHCH_3$, NHAc, $NHC(O)NHCH_3$, or $CH_2NHCH_3$.

In certain embodiments, the T moiety of either of formula I or I-a is a valence bond.

In other embodiments, the T moiety of either of formula I or I-a is —$CH_2$—.

Another embodiment relates to a compound of any of formulae I, I-a, or I-b wherein $R^2$ is selected from $(CH_2)_yR^5$, $(CH_2)_yCH(R^5)_2$, $(CH_2)_yCH(R^6)CH(R^5)_2$, or $(CH_2)_yN(R^4)_2$. According to another embodiment, the $R^2$ group of of any of formulae I, I-a, or I-b is $(CH_2)_yR^5$, $(CH_2)_yCH(R^5)_2$, or $(CH_2)_y$ $CH(R^6)CH(R^5)_2$.

When $R^2$ is $R^5$, $R^5$ groups include an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such groups are pyrrolidin-1-yl, morpholin-4-yl, piperidin-1-yl, and piperazin-1-yl, 4-methyl[1,4]diazepan-1-yl, 4-phenyl-piperazine-1-yl, wherein each group is optionally substituted.

When $R^2$ is $(CH_2)_yR^5$, or $(CH_2)_yCH(R^5)_2$, $R^5$ groups are further selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, $CH_2OH$, $(CH_2)_2OH$, and isopropyl, wherein each group is optionally substituted. Examples of substituents on $R^5$ include OH, pyridyl, piperidinyl, and optionally substituted phenyl.

When $R^2$ is $(CH_2)_nCH(R^5)_2$, $R^5$ groups are selected from $R^3$, $OR^3$, $CO_2R^3$, $(CH_2)N(R^4)_2$, or CN. The $R^5$ group of the $R^2$ moiety of any of formulae I, I-a, or 1-b are also independently selected from $R^3$, $OR^3$, $CO_2R^3$, $(CH_2)N(R^4)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^5$ groups include optionally substituted groups selected from phenyl, pyridyl, morpholin-4-yl, imidazolyl, OH, and $CH_2OH$.

When $R^2$ is $(CH_2)_yCH(R^6)CH(R^5)_2$, $R^6$ groups are selected from $R^3$, $(CH_2)_wOR^3$, or $(CH_2)_wN(R^4)_2$. According to another embodiment, the $R^6$ group of the $R^2$ moiety of any of formulae I, I-a, or I-b is selected from $R^3$ or $(CH_2)_wOR^3$. According to yet another embodiment, the $R^6$ group of the $R^2$ moiety of any of formulae I, I-a, or I-b is selected from OH, $CH_2OH$, $(CH_2)_2OH$. The $R^5$ groups of the $(CH_2)_yCH(R^6)CH$ $(R^5)_2$ moiety are independently selected from $R^3$, $OR^3$, Ar, $CO_2R^3$, $(CH_2)_yN(R^4)_2$, or CN. According to another embodiment, said $R^5$ groups are independently selected from $R^3$, $OR^3$, $CO_2R^3$, $(CH_2)_yN(R^3)_2$, CN, an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur. Examples of such $R^5$ groups include optionally substituted groups selected from phenyl, pyridyl, morpholin-4-yl, imidazolyl, OH, and $CH_2OH$.

According to another embodiment, the $R^y$ groups of any of formulae I, I-a, or I-b, when present, are independently selected from $C_{1-4}$ aliphatic or Ar, wherein Ar is an optionally substituted 3-6 membered saturated, partially unsaturated, or fully unsaturated monocyclic ring having 0-4 heteroatoms independently selected from nitrogen, oxygen, or sulfur, or an optionally substituted 9-10 membered saturated, partially unsaturated, or fully unsaturated bicyclic ring having 0-4 heteroatoms independently selected from nitrogen, oxygen, or sulfur. Another embodiment relates to compounds of any of formulae I, I-a, or I-b wherein the $R^y$ groups are selected from $C_{1-4}$ aliphatic or Ar, wherein Ar is an optionally substituted 5-6 membered saturated, partially unsaturated, or fully unsaturated monocyclic ring having 0-4 heteroatoms independently selected from nitrogen, oxygen, or sulfur. Examples of such groups include phenyl, pyridyl, methyl, cyclohexyl, cyclopentyl, or ethyl.

Another embodiment of the present invention relates to a compound of any of formulae I, I-a, or I-b wherein $R^z$ includes hydrogen, optionally substituted $C_{1-4}$ aliphatic, C(O)R, and C(O)OR. According to another embodiment, $R^z$ is hydrogen, methyl, ethyl, C(O)Me, C(O)OCH$_2$phenyl, and $CH_2$phenyl. According to yet another embodiment, the $R^z$ group of any of formulae I, I-a, or I-b is hydrogen.

According to one embodiment, the Q group of of any of formulae I, I-a, or I-b is selected from —C(O)N(R)— and —C(O)O—. According to another embodiment, Q group of any of formulae I, I-a, or I-b is selected from —C(O)N(H)— and —C(O)O—.

According to one embodiment, the present invention relates to a compound of of any of formulae I, I-a, or I-b wherein Q is —C(O)N(H)—.

According to another embodiment, the present invention relates to a compound of any of formulae I, I-a, or I-b wherein Q is —C(O)O—.

According to yet another embodiment, the present invention relates to a compound of either of formulae I or I-b wherein $T_{(m)}R^1$ is other than hydrogen.

According to another embodiment, the present invention relates to a compound of formula II:

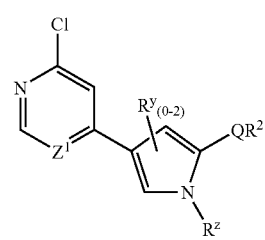

II or a pharmaceutically acceptable salt thereof, wherein $Z^1$, Q, $R^y$, $R^z$, and $R^2$ are as defined above.

Embodiments, and sub-embodiments thereof, relating to the $Z^1$, Q, $R^y$, $R^z$, and $R^2$ groups of formula II are those set forth above for compounds of formulae I, I-a, and I-b.

According to another embodiment, the present invention relates to a compound of formula III:

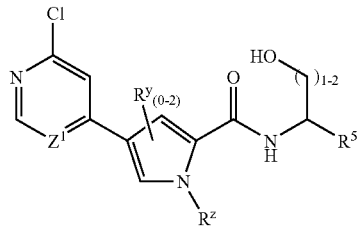

or a pharmaceutically acceptable salt thereof, wherein $Z^1$, $R^y$, $R^z$, and $R^5$ are as defined above.

Embodiments, and sub-embodiments thereof, relating to the $Z^1$, $R^y$, $R^z$, and $R^5$ groups of formula III are those described above for compounds of formulae I, I-a, and I-b.

According to another embodiment, the present invention relates to a compound of formula IV:

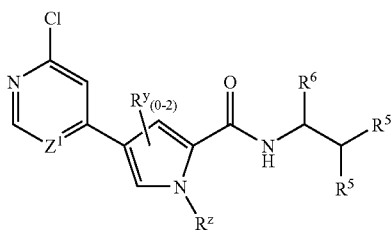

or a pharmaceutically acceptable salt thereof, wherein $Z^1$, $R^y$, $R^z$, $R^5$, and $R^6$ are as defined above.

Embodiments, and sub-embodiments thereof, relating to the $Z^1$, $R^y$, $R^z$, $R^5$, and $R^6$ groups of formula IV are those described above for compounds of formulae I, I-a, and I-b.

Representative compounds of formula I are set forth in Table 1 below.

TABLE 1

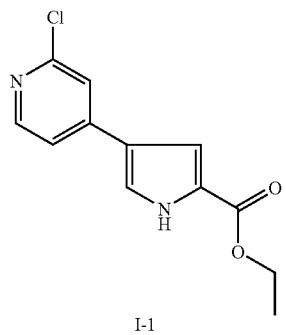

I-1

TABLE 1-continued

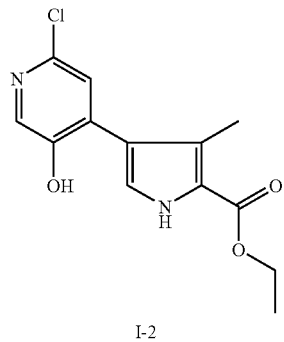

I-2

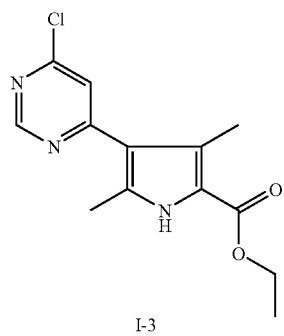

I-3

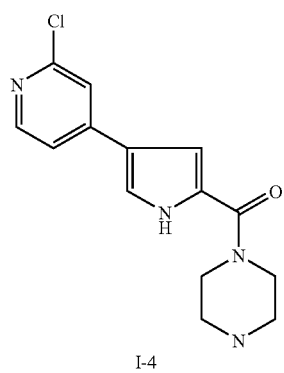

I-4

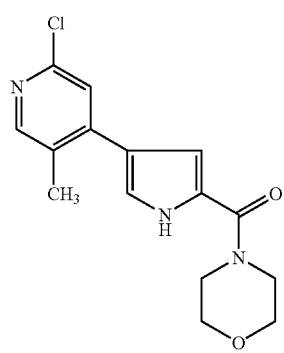

I-5

TABLE 1-continued
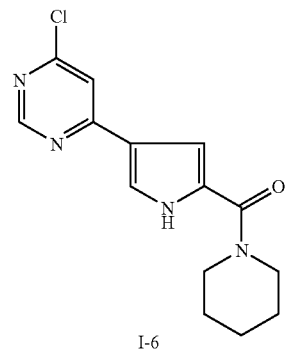
I-6
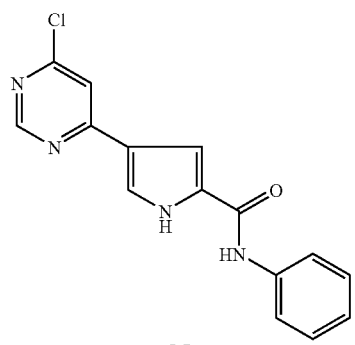
I-7
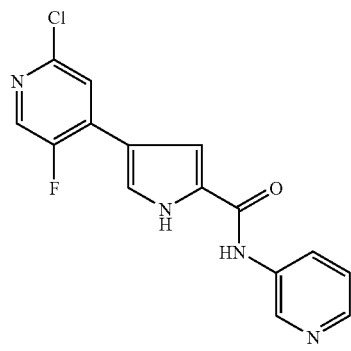
I-8
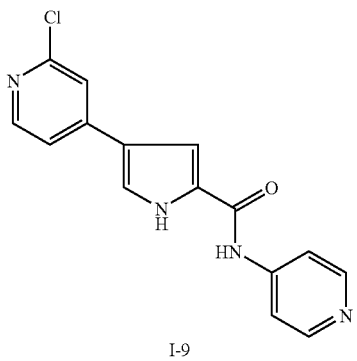
I-9
TABLE 1-continued
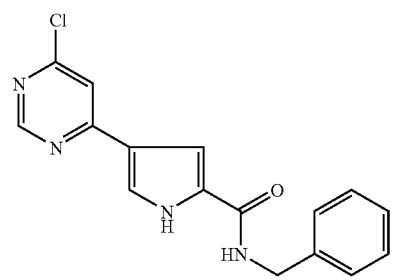
I-10
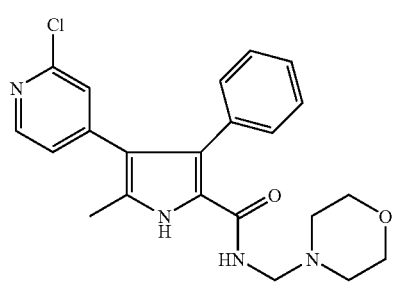
I-11
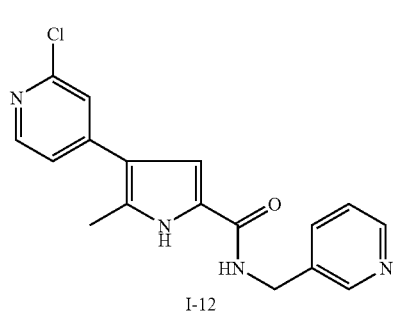
I-12
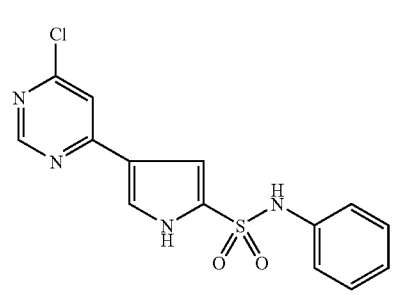
I-13

TABLE 1-continued
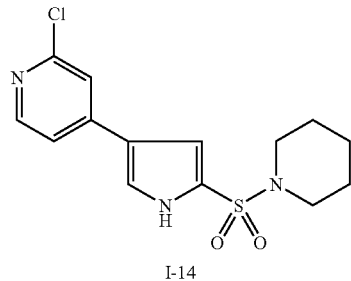
I-14
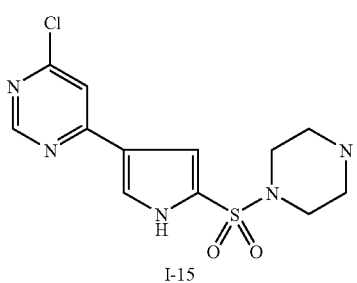
I-15
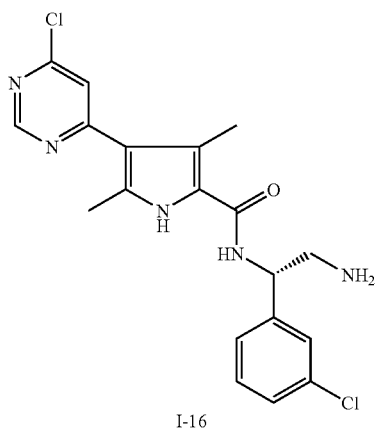
I-16
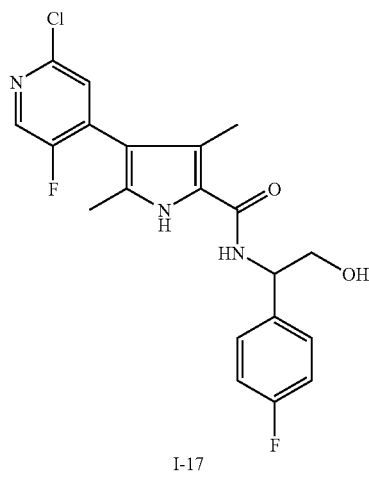
I-17
TABLE 1-continued
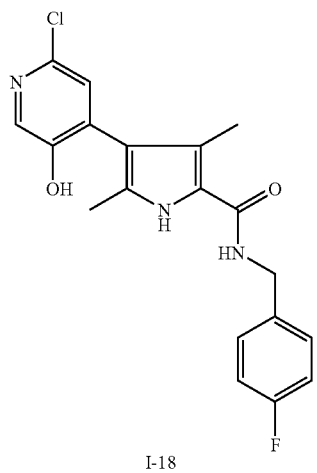
I-18
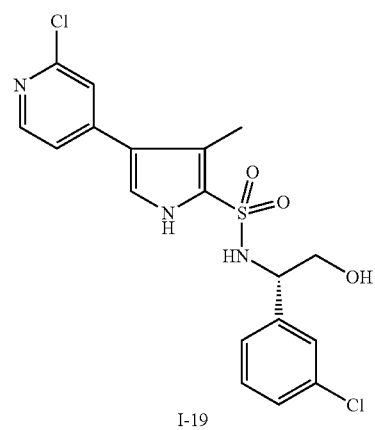
I-19
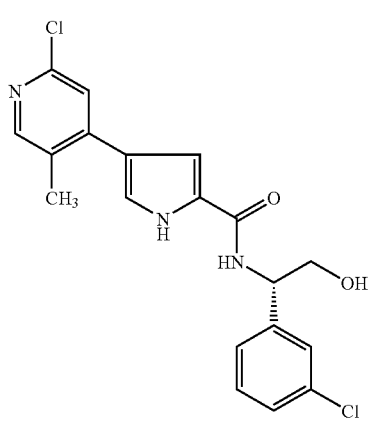
I-20

TABLE 1-continued
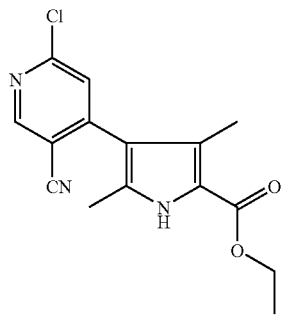
I-21
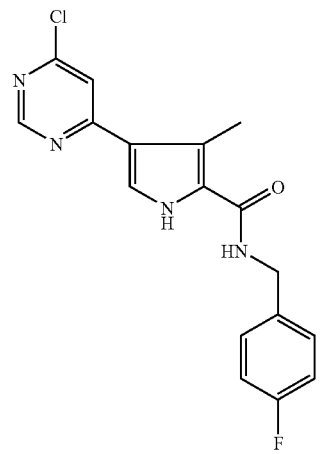
I-24
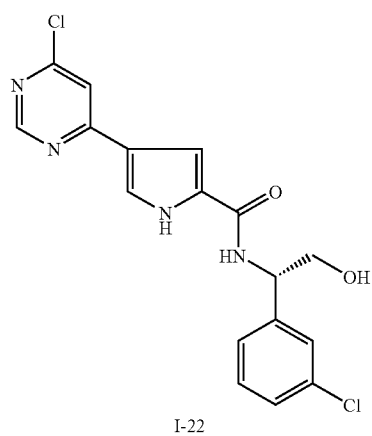
I-22
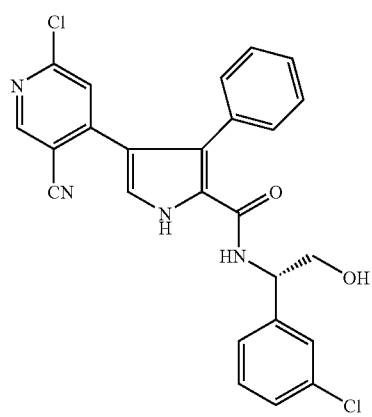
I-25
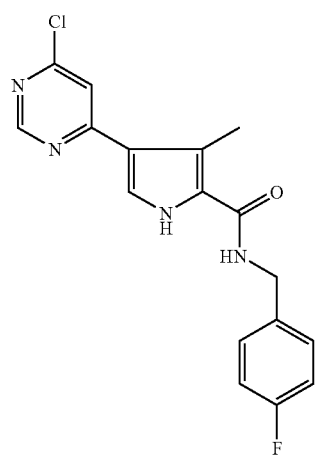
I-23
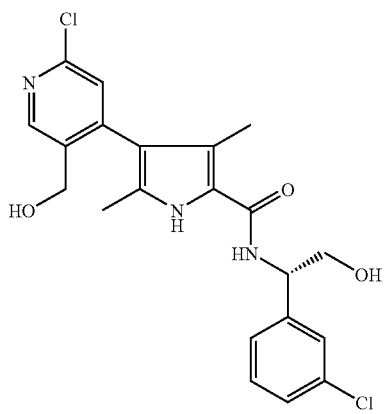
I-26

TABLE 1-continued
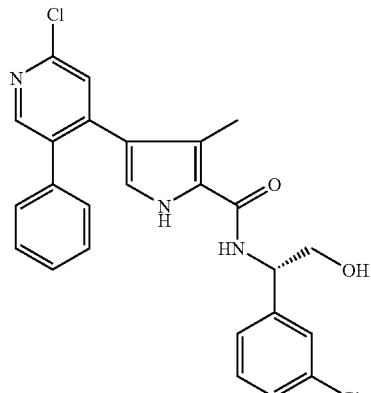
I-27
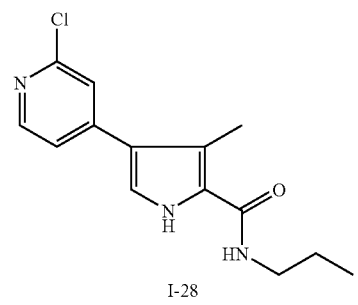
I-28
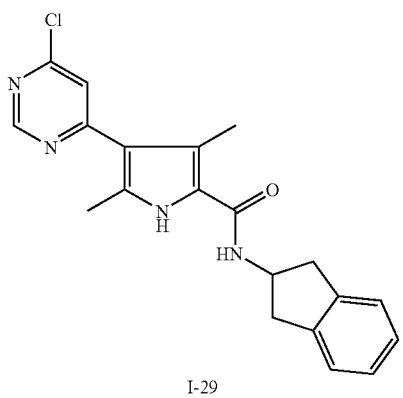
I-29
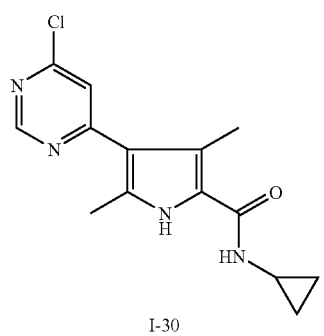
I-30
TABLE 1-continued
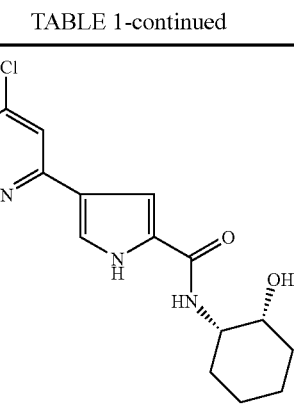
I-31
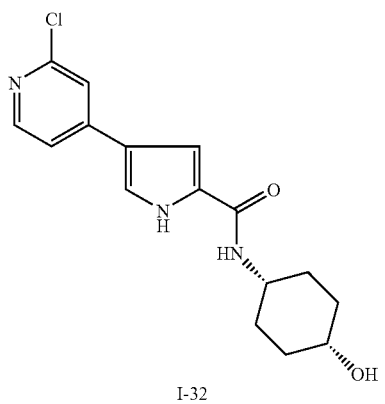
I-32
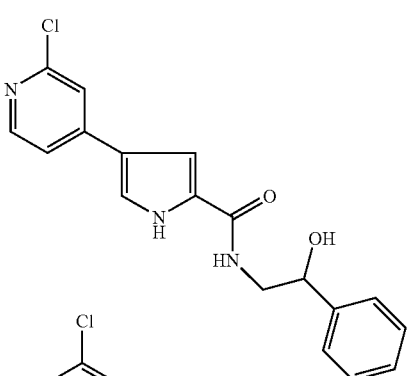
I-33
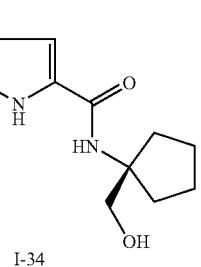
I-34

TABLE 1-continued
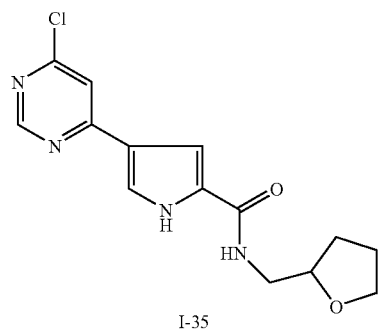
I-35
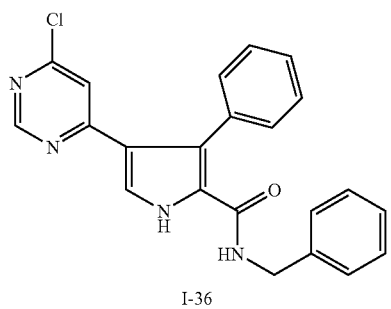
I-36
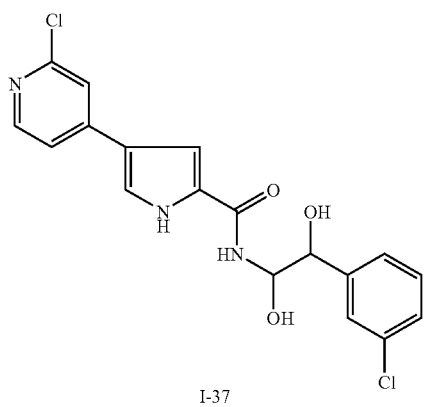
I-37
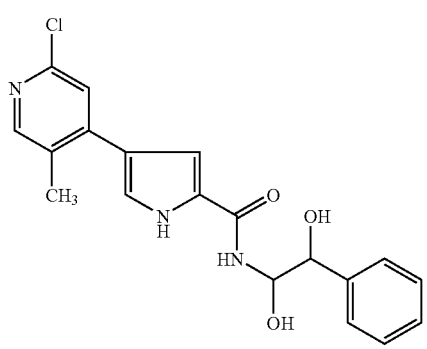
I-38
TABLE 1-continued
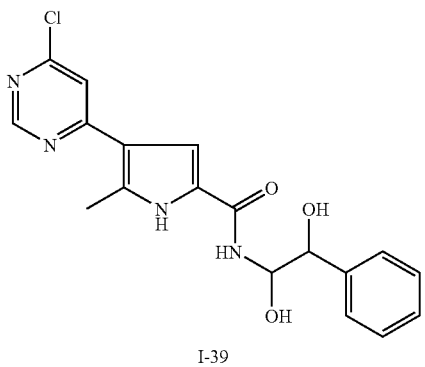
I-39
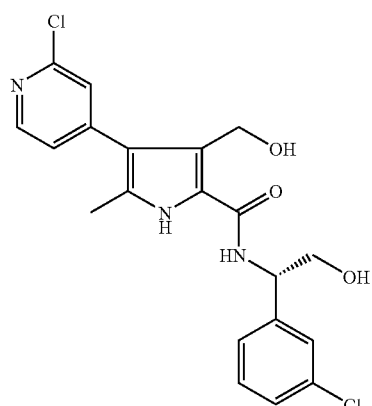
I-40
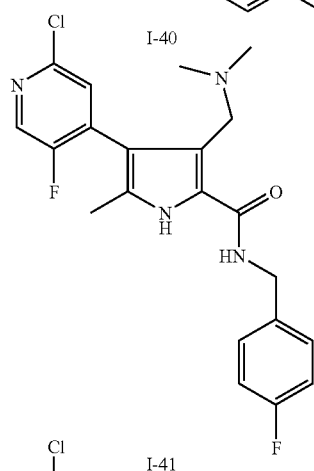
I-41
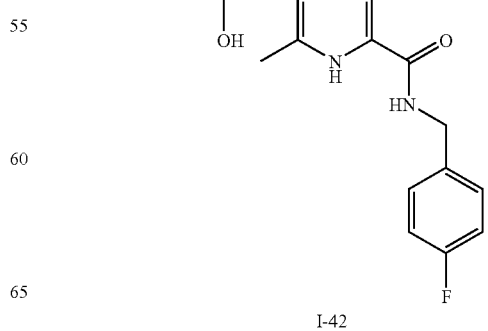
I-42

TABLE 1-continued
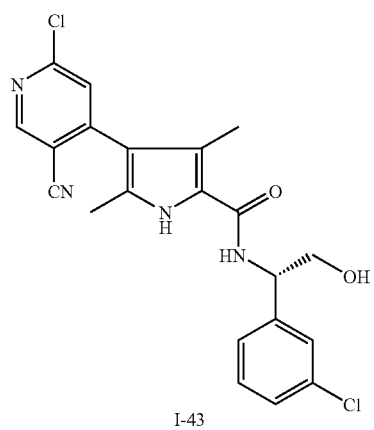
I-43
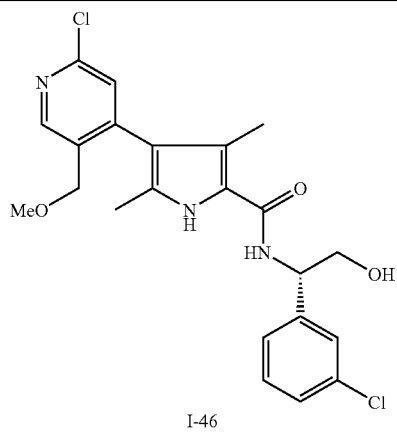
I-46
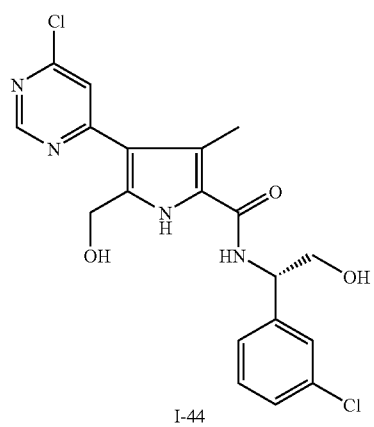
I-44
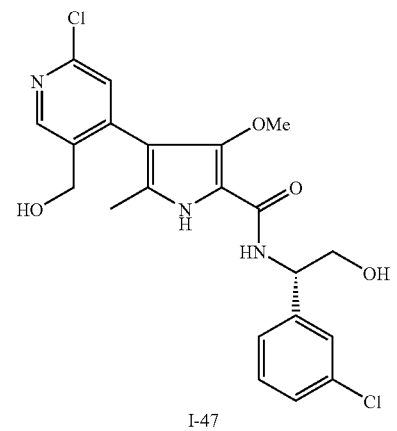
I-47
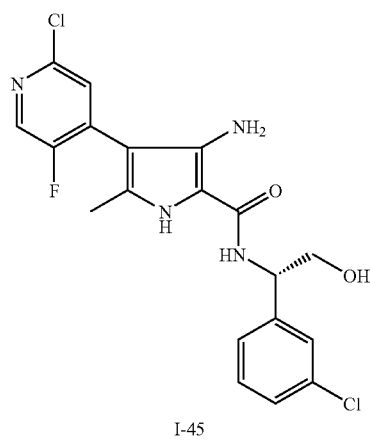
I-45
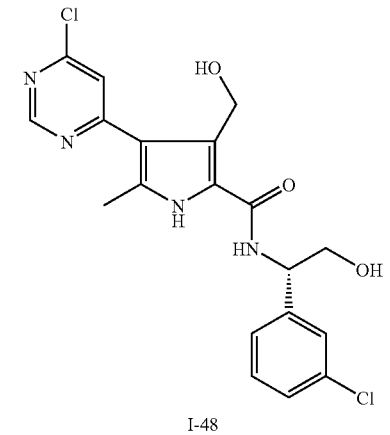
I-48

TABLE 1-continued

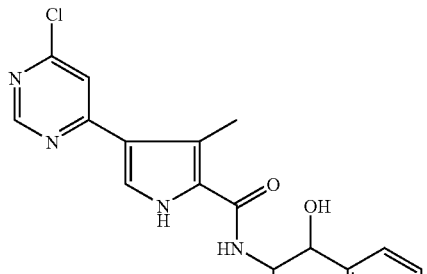

I-49

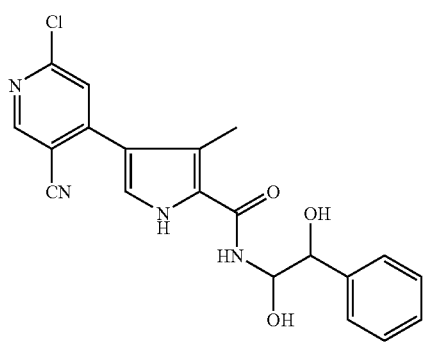

I-50

TABLE 1-continued

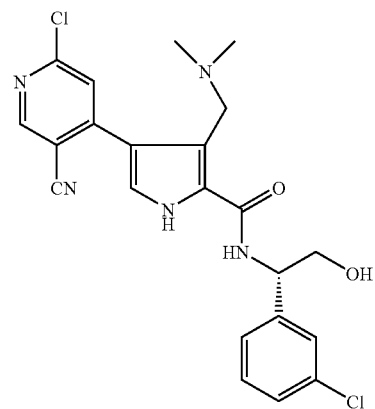

I-51

4. General Methods of Providing the Present Compounds:

The compounds of this invention may be prepared or isolated in general by synthetic and/or pseudo-synthetic methods known to those skilled in the art for analogous compounds and as illustrated by the general Schemes I and II below and the preparative examples that follow.

Scheme I

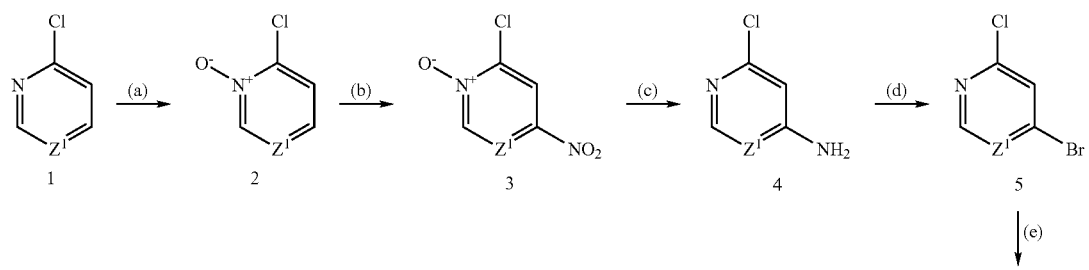

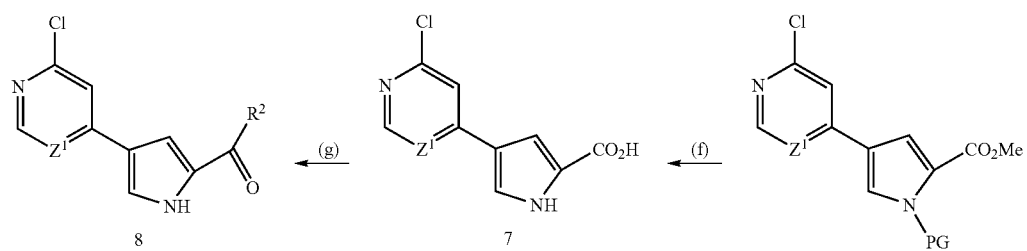

Reagents and conditions: (a) acetic anhydride/H$_2$O$_2$; (b) HNO$_3$/H$_2$SO$_4$; (c) reduction;
(d) bromination; (e) coupling; (f) deprotection/saponification; (g) R$^2$═H, coupling conditions.

Scheme I above depicts a general method for preparing compounds of formula I wherein Q is —C(O)NH—. At step (a), the pyridine/pyrimidine compound 1 is oxidized to form intermediate compound 2 which is then treated with nitric acid to form the nitro compound 3. At step (c), the-nitro group is reduced. One of ordinary skill in the art would recognize that a variety of methods are amenable to the reduction of this nitro group. At step (d), the resulting amino moiety is displaced by bromine to form compound 5. This bromo intermediate is then coupled to an appropriately protected pyrrole moiety to form compound 6. One of skill in the art would recognize that a variety of protecting groups are suitable for the above reaction. Amino protecting groups are well known in the art and are described in detail in *Protecting Groups in Organic Synthesis*, Theodora W. Greene and Peter G. M. Wuts, 1991, published by John Wiley and Sons, the entirety of which is hereby incorporated by reference.

At step (f), the pyrrolyl protecting group is removed and the ester saponified to form compound 7. The carboxyl moiety of compound 7 may then be coupled to a variety of amines to form compounds of the present invention where Q is —C(O)NH—. Alternatively, one of ordinary skill in the art would recognize that a variety of compounds of the present invention are readily obtained from the carboxylic acid compound 7. For example, compound 7 is coupled with a variety of amines to prepare the amide compounds depicted or, alternatively, with a variety of alcohols to prepare compounds of the present invention wherein Q is —C(O)O—.

be considered as limiting the scope of said invention. Details of the reactions set forth in Scheme II are provided in the Examples below.

Although certain exemplary embodiments are depicted and described above and herein, it will be appreciated that compounds of the invention can be prepared according to the methods described generally above using appropriate starting materials by methods generally available to one of ordinary skill in the art.

5. Uses, Formulation, and Administration

Pharmaceutically Acceptable Compositions

As discussed above, the present invention provides compounds that are inhibitors of protein kinases, and thus the present compounds are useful for the treatment of diseases, disorders, and conditions including, but not limited to cancer, autoimmune disorders, neurodegenerative and neurological disorders, schizophrenia, bone-related disorders, liver disease, and cardiac disorders. Accordingly, in another aspect of the present invention, pharmaceutically acceptable compositions are provided, wherein these compositions comprise any of the compounds as described herein, and optionally comprise a pharmaceutically acceptable carrier, adjuvant, or vehicle. In certain embodiments, these compositions optionally further comprise one or more additional therapeutic agents.

It will also be appreciated that certain of the compounds of present invention can exist in free form for treatment, or

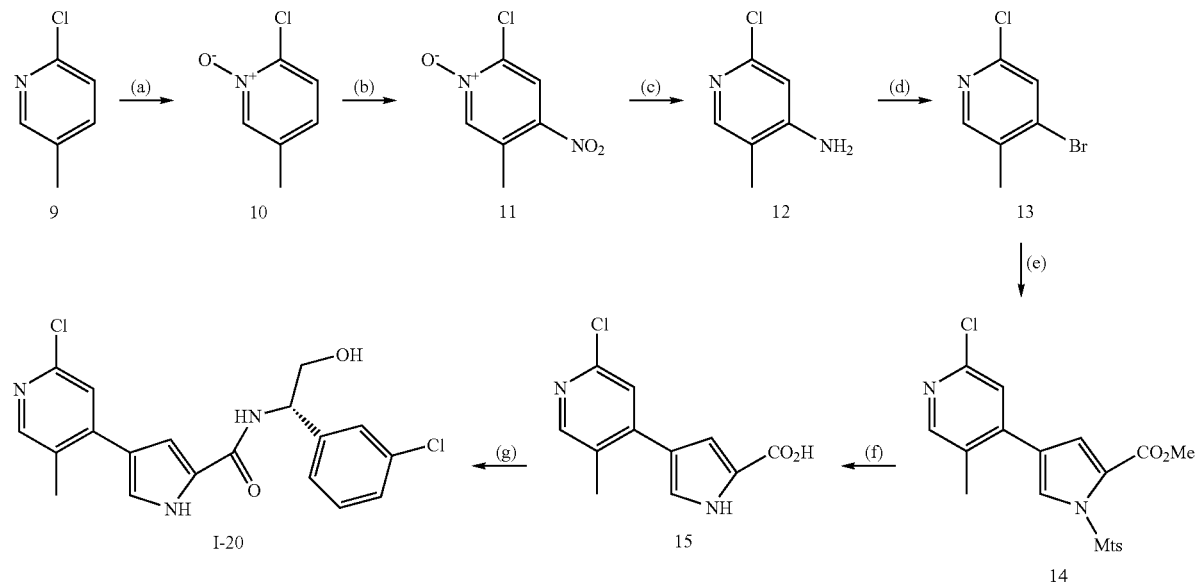

Reagents and conditions: (a) acetic anhydride/$H_2O_2$; (b) $HNO_3/H_2SO_4$; (c) Fe/acetic acid; (d) $CuBr_2$/t-BuONO in acetonitrile; (e) 4-(4,4,5,5-tetramethyl-[1,3,2]dioxaborolan-2-yl)-1-(2,4,6-trimethylbenzensulfonyl-1H-pyrrole-2-carboxylic acid methyl ester and $Pd(PPh_3)_4/Na_2CO_3$ in benzene; (f) NaOH/MeOH; (g) (S)-3-chlorophenylglycinol-HCl, EDCI/HOBt, DMF/DIEA.

Using the preparation of compound I-20 to illustrate, Scheme II depicts a representative synthesis for the preparation of compounds of the present invention and is in no way to where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of ERK2 or ROCK protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}$ $alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of cancer, an autoimmune disorder, a neurodegenerative or neurological disorder, schizophrenia, a bone-related disorder, liver disease, or a cardiac disorder is provided comprising administering an effective amount of a compound of the present invention, or a pharmaceutically acceptable composition comprising a compound of the present invention, to a subject in need thereof. In certain embodiments of the present invention an "effective amount" of the compound or pharmaceutically acceptable composition is that amount effective for treating or lessening the severity of a disease, condition, or disorder selected from cancer, an autoimmune disorder, a neurodegenerative or neurological disorder, schizophrenia, a bone-related disorder, liver disease, or a cardiac disorder. The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of ERK2 or ROCK protein kinases and thus, without wishing to be bound by any particular theory, the compounds and compositions are particularly useful for treating or lessening the severity of a disease, condition, or disorder where activation of one or more of ERK2 or ROCK protein kinases is implicated in the disease, condition, or disorder. When activation of ERK2 or ROCK protein kinases is implicated in a particular disease, condition, or disorder, the disease, condition, or disorder may also be referred to as "ERK2- or ROCK-mediated disease", condition, or disease symptom. Accordingly, in another aspect, the present invention provides a method for treating or lessening the severity of a disease, condition, or disorder where activation or one or more of ERK2 or ROCK protein kinases is implicated in said disease, condition, or disorder.

The activity of a compound utilized in this invention as an inhibitor of ERK2 or ROCK protein kinases may be assayed in vitro, in vivo or in a cell line. In vitro assays include assays that determine inhibition of either the phosphorylation activity or ATPase activity of activated ERK2 or ROCK protein kinases. Alternate in vitro assays quantitate the ability of the inhibitor to bind to ERK2 or ROCK protein kinases. Inhibitor binding may be measured by radiolabelling the inhibitor prior to binding, isolating the inhibitor/ERK2 or inhibitor/ROCK complex and determining the amount of radiolabel bound. Alternatively, inhibitor binding may be determined by running a competition experiment where new inhibitors are incubated with ERK2 or ROCK protein kinases bound to known radioligands.

The term "measurably inhibit", as used herein means a measurable change in ERK2 or ROCK protein kinase activity between a sample comprising said composition and a ERK2 or ROCK protein kinase and an equivalent sample comprising ERK2 or ROCK protein kinase in the absence of said composition. Such measurements of protein kinase activity are known to one of ordinary skill in the art and include those methods set forth herein below.

According to another embodiment, the invention relates to a method of inhibiting ERK2 or ROCK protein kinase activity in a patient comprising the step of administering to said patient a compound of the present invention, or a composition comprising said compound.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction.

Accordingly, another embodiment of the present invention relates to treating or lessening the severity of one or more diseases in which ROCK is known to play a role. Specifically, the present invention relates to a method of treating or lessening the severity of a disease or condition selected from hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction, wherein said method comprises administering to a patient in need thereof a composition according to the present invention.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, Velcade®, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids, or combinations thereof to impart controlled release characteristics in the composition.

Another aspect of the invention relates to inhibiting ERK2 or ROCK protein kinase activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition of ERK2 or ROCK protein kinase activity in a biological sample is useful for a variety of purposes that are known to one of skill in the art. Examples of such purposes include, but are not limited to, blood transfusion, organ-transplantation, biological specimen storage, and biological assays.

SYNTHETIC EXAMPLES

As used herein, the term "$R_t$" refers to the retention time, in minutes, associated with the compound using the following HPLC method:

Column: YMC ODS-AQ 55 120A column with a size of 3.0×150 mm

Gradient: water:MeCN, 0.1% TFA (90:10→0:100) over 8 minutes

Flow rate: 1 mL/min

Wavelength: 214 nm.

Unless otherwise indicated, each $^1$H NMR was obtained at 500 MHz and compound numbers correspond to those compound numbers recited in Table 1.

Example 1

2-Chloro-5-methyl-4-nitropyridine N-oxide: In a manner substantially similar to that of of Z. Talik and A. Puszko, *Roczniki Chemii Ann. Soc. Chim. Polonorum* 1976, 50, 2209, hydrogen peroxide 30% (25 mL) was added in small portions to a suspension of 2-chloro-5-methylpyridine (10 g, 0.078 mol) in acetic anhydride (25 mL). This mixture was stirred at room temperature for 24 hours and then heated at 60° C. for 30 hours. After removing excess acetic acid under reduced pressure, the residue was added in small portions to concentrated sulfuric acid (15 mL). The resulting solution was added to a mixture of concentrated sulfuric acid (15 mL) and fuming nitric acid (25 mL) and then heated at 100° C. for 90 minutes. The reaction mixture was poured on ice, neutralized with solid ammonium carbonate and finally with aqueous ammonia until pH basic, resulting in the formation of a precipitate. After filtration, the title compound was isolated as a pale yellow solid (9.4 g, 0.050 mol, HPLC $R_t$ 3.272 min, FIA ES+188.9, ES–188.0).

Example 2

4-Amino-2-chloro-5-methylpyridine: Iron (1.0 g) was added to a solution of 2-chloro-5-methyl-4-nitropyridine N-oxide (500 mg, 2.6 mmol) in glacial acetic acid (10 mL).

The reaction mixture was then heated at 100° C. for 20 minutes. The suspension was poured onto aqueous NaOH (1M) and extracted with ethyl acetate. After drying over Na$_2$SO$_4$, the solvent was then evaporated and the title compound was isolated as a colorless solid (370 mg, 2.6 mmol, HPLC R$_t$ 1.3 min, FIA ES+ 143.0).

Example 3

4-Bromo-2-chloro-5-methylpyridine: CuBr$_2$ (984 mg, 4.4 mmol, 2.0 equiv.) and tert-butylnitrite (0.5 mL) were mixed in acetonitrile (4 mL). The resulting mixture was heated at 65° C. for 20 minutes and 4-amino-2-chloro-5-methylpyridine (320 mg, 2.2 mmol, 1.0 equivalent) was then added and the resulting mixture was stirred for 10 minutes at 65° C. The reaction mixture was poured on water and extracted with ethyl acetate. The organic layer was washed with NH$_4$OH until no blue color was observed in the aqueous layer. After washing with water, the organic extract was dried over Na$_2$SO$_4$ and the solvent was removed under reduced pressure. The crude residue was purified by preparative TLC on SiO$_2$ (dichloromethane) to afford the title compound as a colorless oil (170 mg, 0.8 mmol, HPLC R$_t$ 6.709 min, FIA ES+205.9, 207.9, ES–205.9).

Example 4

4-(2-Chloro-5-methylpyridin-4-yl)-1-(2,4,6-trimethylbenzensulfonyl)-1H-pyrrole-2-carboxylic acid methyl ester: 4-(4,4,5,5-Tetramethyl-[1,3,2]dioxaborolan-2-yl)-1-(2,4,6-trimethylbenzensulfonyl)-1H-pyrrole-2-carboxylic acid methyl ester (125 mg, 0.29 mmol, 0.6 equiv.) and 4-bromo-2-chloro-5-methylpyridine (96 mg, 0.47 mmol, 1.0 equiv.) were dissolved in benzene (4 mL). After adding methanol (0.94 mL) and aqueous Na$_2$CO$_3$, Pd(PPh$_3$)$_4$ (108 mg, 0.094 mol, 0.2 equiv.) was then added and the resulting mixture was heated at reflux for 16 hours. The reaction mixture was dissolved in ethyl acetate and washed with water. After drying the organic layer over Na$_2$SO$_4$, the solvent was removed under reduced pressure. The crude material was purified by reversed phase HPLC (acetonitrile/water/TFA), yielding the title compound as a colorless solid (54 mg, 0.125 mmol, HPLC R$_t$ 9.087 min, ES+433.0, ES–431.0).

Example 5

4-(2-Chloro-5-methylpyridin-4-yl)-1H-pyrrole-2-carboxylic acid [1-(S)-(3-chlorophenylgylcinol] amide (1-20): 4-(2-Chloro-5-methylpyridin-4-yl)-1-(2,4,6-trimethylbenzensulfonyl)-1H-pyrrole-2-carboxylic acid methyl ester (190 mg, 0.44 mmol, crude material, 1.0 equiv.) was dissolved in methanol (2 mL). A solution of 1 M aqueous NaOH (2 mL) was then added and the resulting mixture was refluxed for 3 hours. The reaction mixture was neutralized with aqueous 1 M HCl and extracted with ethyl acetate. After drying the organic layer over Na$_2$SO$_4$, the solvent was removed under reduced pressure. The crude material was then dissolved in DMF (3 mL) and EDCI (103 mg, 0.54 mmol, 1.2 equiv.), HOBt (73 mg, 0.54 mmol, 1.2 equiv) and DIEA (0.22 mL, 1.3 mmol, 3 equiv.) were added. The reaction mixture was stirred for 30 minutes at room temperature. (S)-3-Chlorophenylglycinol HCl salt (183 mg, 0.88 mmol, 2.0 equiv.) was added and the reaction mixture was then stirred for 16 hours at room temperature. The crude reaction mixture was then dissolved in ethyl acetate. After washing with water, the organic extract was dried over Na$_2$SO$_4$ and the solvent was removed under reduced pressure. The crude residue was purified by preparative TLC on SiO$_2$ (DCM/methanol 95:5) to afford the title compound as a colorless solid (31 mg, 0.08 mmol, HPLC R$_t$ 5.880 minutes; FIA ES+390.0, ES–388.1; LC/MS R$_t$ 3.3 minutes, ES+390.0, ES–388.1; $^1$HNMR (CD$_3$OD) d 2.45 (s, 3H), 3.8 (d, 2H), 5.1 (t, 1H), 7.4 (m, 6H), 7.48 (s, 1H), 8.15 (s, 1H).

Biological Testing

The activity of the present compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands. The details of the conditions used for performing these assays are set forth in Examples 6-9.

Example 6

ERK2 Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM MgCl$_2$, 2.5 mM phosphoenolpyruvate, 200 µM NADH, 150 µg/mL pyruvate kinase, 50 µg/mL lactate dehydrogenase, and 200 µM erktide peptide. The reaction was initiated by the addition of 65 µM ATP. The rate of decrease of absorbance at 340 nM was monitored. The K$_i$ and IC$_{50}$ were evaluated from the rate data as a function of inhibitor concentration.

Example 7

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 µCi/mL in RPMI medium then 20 µL of this solution is added to each well. The plates are further incubated at 37° C. for 8 hours then harvested and analyzed for $^3$H-thymidine uptake using a liquid scintillation counter.

Example 8

ERK1 Inhibition Assay

Compounds may be assayed for the inhibition of ERK1 by a spectrophotometric coupled-enzyme assay (Fox et al (1998) *Protein Sci* 7, 2249). In this assay, a fixed concentration of activated ERK1 (20 nM) is incubated with various concentrations of the compound in DMSO (2.0%) for 10 min. at 30° C. in 0.1 M HEPES buffer, pH 7.6, containing 10 mM $MgCl_2$, 2.5 mM phosphoenolpyruvate, 200 µM NADH, 30 µg/mL pyruvate kinase, 10 µg/mL lactate dehydrogenase, and 150 µM erktide peptide. The reaction is initiated by the addition of 140 µM ATP (20 µL). The rate of decrease of absorbance at 340 nM is monitored. The $K_i$ is evaluated from the rate data as a function of inhibitor concentration.

Example 9

ROCK Inhibition Assay

Compounds may be screened for their ability to inhibit ROCK using a standard coupled enzyme assay (Fox et al., *Protein Sci.* 1998, 7, 2249). Reactions are carried out in 100 mM HEPES pH 7.5, 10 mM MgCl2, 25 mM NaCl, 1 mM DTT and 1.5% DMSO. Final substrate concentrations in the assay are 13 µM ATP (Sigma chemicals) and 200 µM peptide (American Peptide, Sunnyvale, Calif.). Assays are carried out at 30° C. and 200 nM ROCK. Final concentrations of the components of the coupled enzyme system are 2.5 mM phosphoenolpyruvate, 400 µM NADH, 30 µg/mL pyruvate kinase and 10 µg/mL lactate dehydrogenase.

An assay stock buffer solution is prepared containing all of the reagents listed above, with the exception of ROCK, DTT, and the test compound of interest. 56 µL of the test reaction is placed in a 384 well plate followed by addition of µL of 2 mM DMSO stock containing the test compound (final compound concentration 30 µM). The plate is preincubated for about 10 minutes at 30° C. and the reaction initiated by addition of 10 µL of enzyme (final concentration 100 nM). Rates of reaction are obtained using a BioRad Ultramark plate reader (Hercules, Calif.) over a 5 minute read time at 30° C.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of formula II:

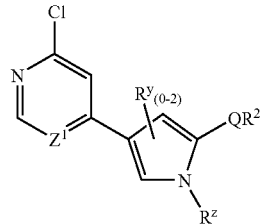

or a pharmaceutically acceptable salt thereof, wherein:
each $R^y$ is independently selected from an optionally substituted $C_{1-6}$ aliphatic group, Ar, CN, $NO_2$, halogen, $N(R)_2$, SR, or OR, provided that two $R^y$ groups are not simultaneously Ar;
$R^z$ is R, C(O)R, C(O)OR, or $SO_2R$;
$Z^1$ is $C-T_{(m)}R^1$;
T is a valence bond or a $C_{1-6}$ alkylidene chain;
m is zero or one;
$R^1$ is selected from CN, halogen, $OR^3$, $SR^3$, $N(R)R^3$, or $R^4$;
Q is selected from a valence bond, —C(O)N(R)—, —$SO_2$N(R)—, —$SO_2$—, —N(R)C(O)N(R)—, —N(R)C(O)—, —N(R)$SO_2$—, —N(R)$SO_2$N(R)—, —N(R)C(O)O—, —C(O)—, or —C(O)O—;
$R^2$ is selected from halogen, CN, $(CH_2)_yR^5$, $(CH_2)_yCH(R^5)_2$, $(CH_2)_yCH(R^6)CH(R^5)_2$, $(CH_2)_yN(R^4)_2$, or $N(R^4)(CH_2)_yN(R^4)_2$;
each $R^3$ is independently selected from R or Ar;
each y is independently 0-6;
each Ar is independently selected from an optionally substituted 3-7 membered saturated, partially unsaturated, or fully unsaturated monocyclic ring having 0-4 heteroatoms independently selected from nitrogen, oxygen, or sulfur, or an optionally substituted 8-10 membered saturated, partially unsaturated, or fully unsaturated bicyclic ring having 0-4 heteroatoms independently selected from nitrogen, oxygen, or sulfur;
each R is independently selected from hydrogen or an optionally substituted $C_{1-6}$ aliphatic group, or:
two R on the same nitrogen atom are taken together with the nitrogen atom attached thereto to form a 4-8 membered saturated, partially unsaturated, or fully unsaturated ring having 1-4 heteroatoms independently selected from nitrogen, oxygen, or sulfur;
each $R^4$ is independently selected from $R^3$, $C(O)R^3$, $CO_2R^3$, $CON(R^3)_2$, $SO_2R^3$;
each $R^5$ is independently selected from $R^3$, $OR^3$, $C_2R^3$, $(CH_2)_yN(R^4)_2$, $N(R^4)_2$, $N(R)C(O)R^3$, $N(R)CON(R^3)_2$, $CON(R^3)_2$, $SO_2R^3$, $N(R)SO_2R^3$, $C(O)R^3$, CN, or $SO_2N(R^3)_2$;
$R^6$ is selected from $R^3$, $(CH_2)_wOR^3$, $(CH_2)_wN(R^4)_2$, or $(CH_2)_wSR^3$; and
each w is independently selected from 0-4.
2. The compound according to claim 1, wherein $R^1$ is selected from hydrogen, $N(R)R^3$, $OR^3$, 3-6 membered carbocyclyl, or an optionally substituted group selected from $C_{1-6}$ aliphatic or a 5-6 membered aryl ring having 0-4 heteroatoms independently selected from nitrogen, oxygen, or sulfur.
3. The compound according to claim 1, wherein T is a valence bond.
4. The compound according to claim 1, wherein T is —$CH_2$—.

5. The compound according to claim 1, wherein $R^2$ is selected from $(CH_2)_yR^5$, $(CH_2)_yCH(R^5)_2$, $(CH_2)_yCH(R^6)CH(R^5)_2$, or $(CH_2)_yN(R^4)_2$.

6. The compound according to claim 5, wherein each $R^5$ is independently selected from an optionally substituted 5-6 membered saturated, partially unsaturated, or fully unsaturated ring having 0-4 heteroatoms independently selected from nitrogen, oxygen, or sulfur, or an optionally substituted 9-10 membered saturated, partially unsaturated, or fully unsaturated ring having 0-4 heteroatoms independently selected from nitrogen, oxygen, or sulfur.

7. The compound according to claim 5, wherein each $R^5$ is independently selected from $R^3$, $OR^3$, $CO_2R^3$, $(CH_2)N(R^4)_2$, or CN.

8. The compound according to claim 1, wherein said compound is of formula III:

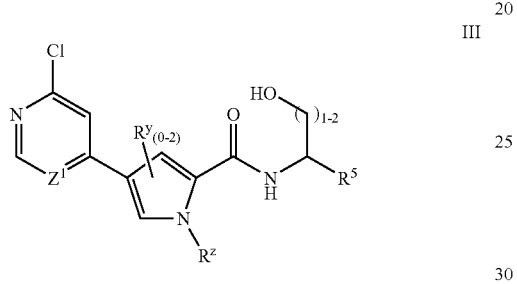

III or a pharmaceutically acceptable salt thereof.

9. The compound according to claim 1, wherein said compound is of formula IV:

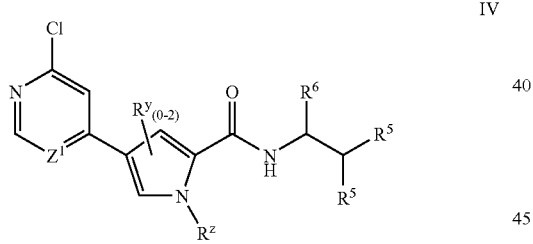

IV or a pharmaceutically acceptable salt thereof.

10. The compound according to claim 1 selected from the group consisting of:

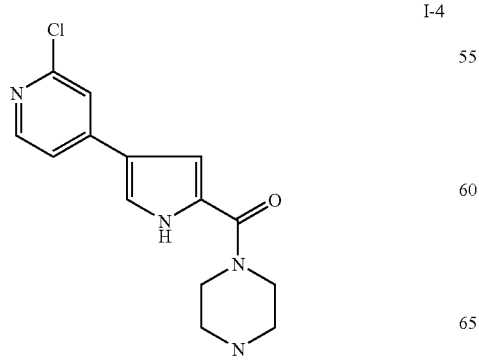

I-4

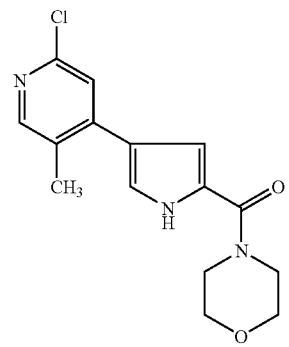

I-5

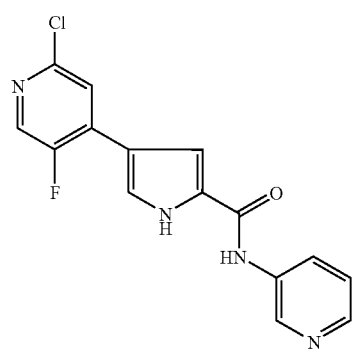

I-8

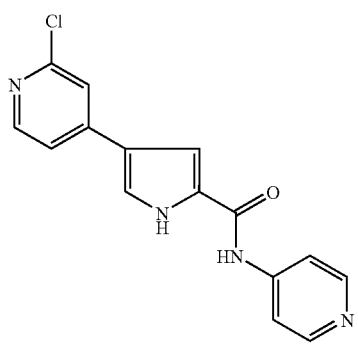

I-9

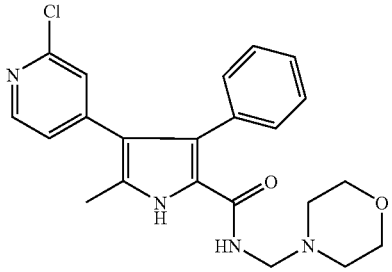

I-11

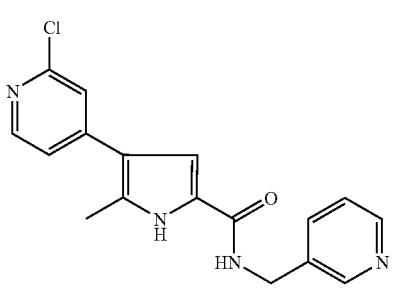

I-12

I-14
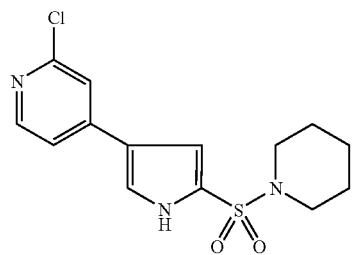
I-17
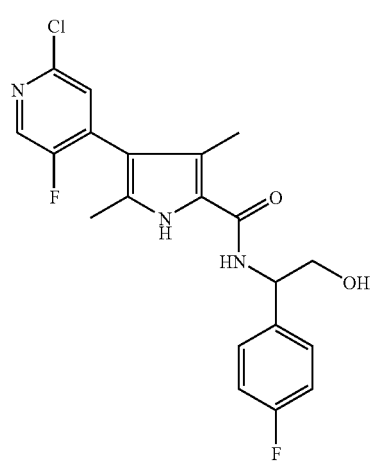
I-18
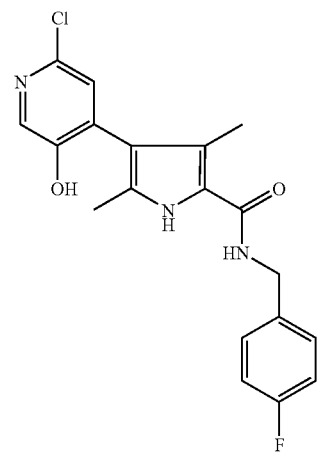
I-19
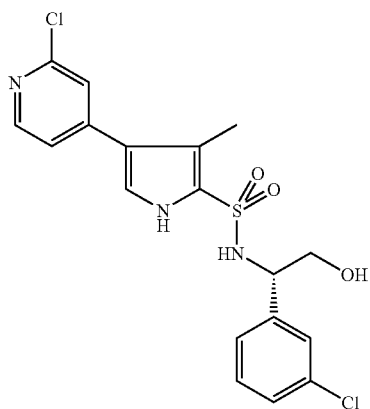
I-20
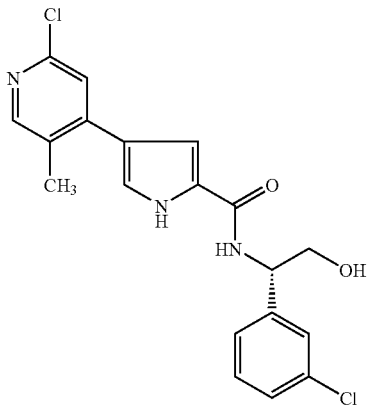
I-21
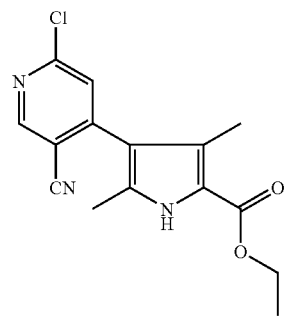
I-25
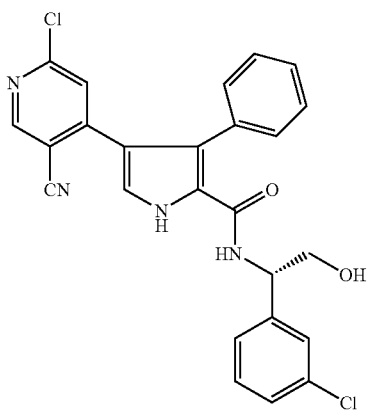
I-26
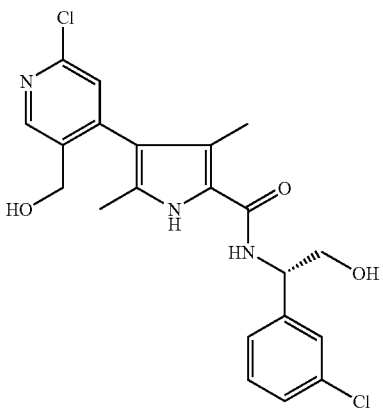

-continued
I-27
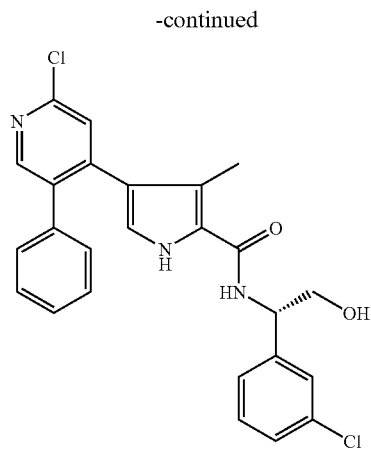
I-28
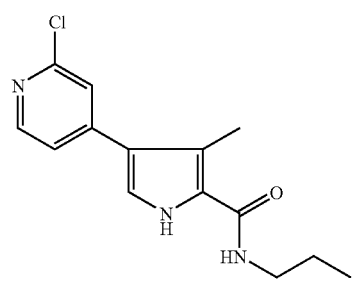
I-32
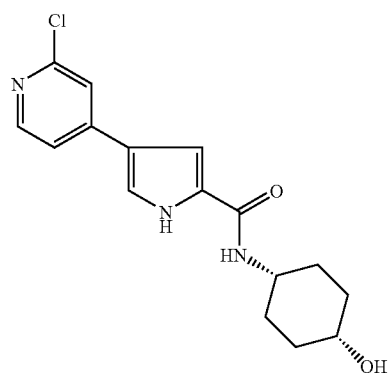
I-33
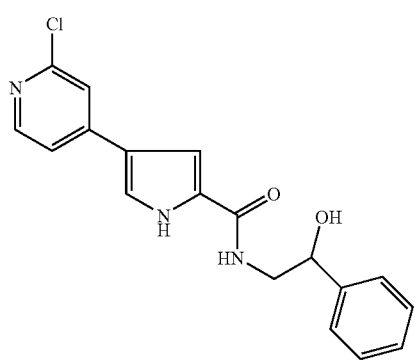
-continued
I-37
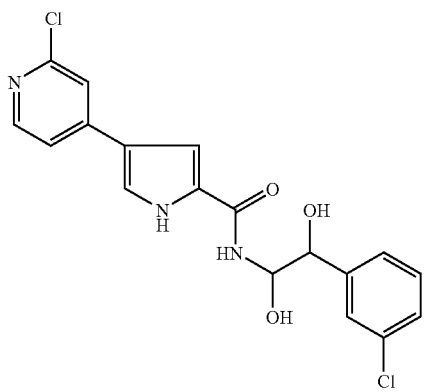
I-38
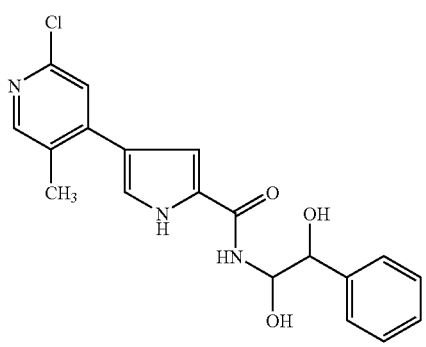
I-40
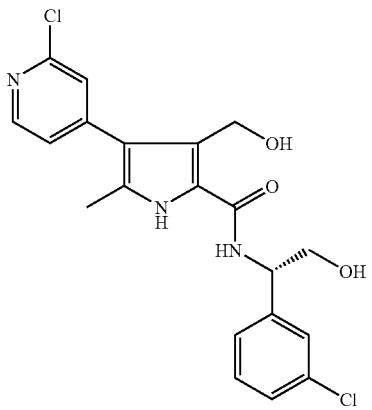
I-41
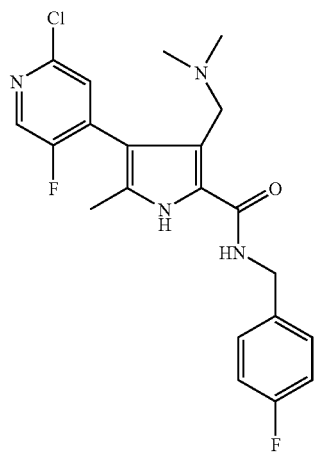

-continued
I-42
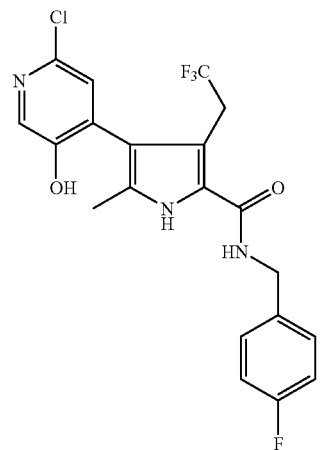
I-43
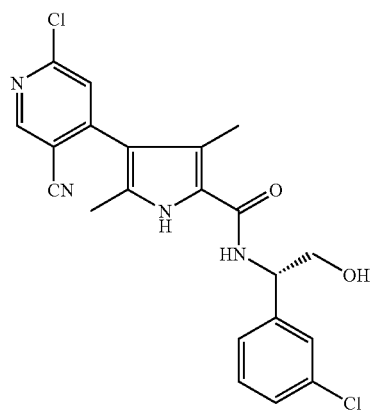
I-45
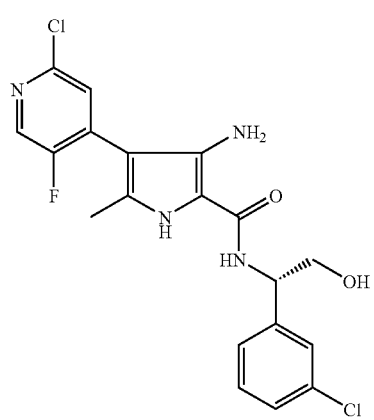
-continued
I-46
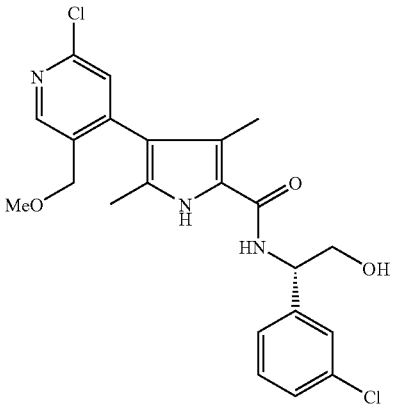
I-47
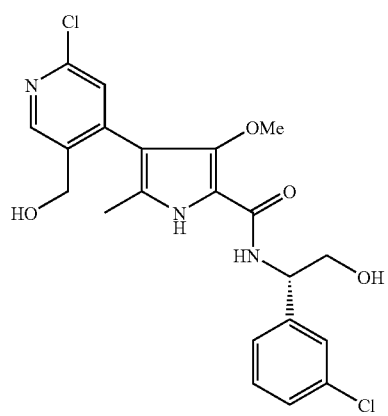
I-50
and
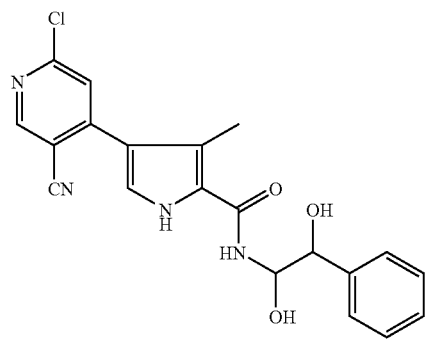

-continued

I-51

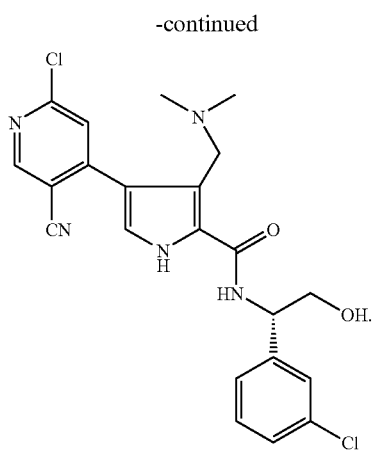

11. A composition comprising a compound according to claim 1, and a pharmaceutically acceptable carrier, adjuvant, or vehicle.

12. The composition of claim 11, additionally comprising a therapeutic agent selected from a chemotherapeutic or antiproliferative agent.

13. A method of treating or lessening the severity of colon cancer, in a patient in need thereof comprising the step of administering to said patient a composition according to claim 11.

14. The method according to claim 13, comprising the additional step of administering to said patient an additional therapeutic agent selected from a chemotherapeutic or antiproliferative agent, wherein:
  (a) said additional therapeutic agent is appropriate for the disease being treated; and
  (b) said additional therapeutic agent is administered together with said composition as a single dosage form or separately from said composition as part of a multiple dosage form.

15. A composition for coating an implantable device comprising a compound according to claim 1 and a carrier suitable for coating said implantable device.

* * * * *